United States Patent
Bernhard (10) Patent No.: US 10,111,734 B2
(45) Date of Patent: Oct. 30, 2018

(54) DENTAL KIT-OF-PARTS AND METHOD OF ASSEMBLING THE SAME

(71) Applicant: NOBEL BIOCARE SERVICES AG, Kloten (CH)

(72) Inventor: Nicolai Bernhard, Winterthur (CH)

(73) Assignee: NOBEL BIOCARE SERVICES AG, Kloten (CH)

( * ) Notice: Subject to any disclaimer, the term of this patent is extended or adjusted under 35 U.S.C. 154(b) by 106 days.

(21) Appl. No.: 15/026,559

(22) PCT Filed: Sep. 25, 2014

(86) PCT No.: PCT/EP2014/070443
§ 371 (c)(1),
(2) Date: Mar. 31, 2016

(87) PCT Pub. No.: WO2015/049149
PCT Pub. Date: Apr. 9, 2015

(65) Prior Publication Data
US 2016/0242877 A1    Aug. 25, 2016

(30) Foreign Application Priority Data
Oct. 1, 2013    (GB) .................................. 1317400.8

(51) Int. Cl.
*A61C 13/00*    (2006.01)
*A61C 8/00*    (2006.01)
(Continued)

(52) U.S. Cl.
CPC ............ *A61C 8/0068* (2013.01); *A61C 8/005* (2013.01); *A61C 8/0016* (2013.01);
(Continued)

(58) Field of Classification Search
CPC ..... A61C 8/0068; A61C 8/0016; A61C 8/005; A61C 8/0089; A61C 13/0013;
(Continued)

(56) References Cited

U.S. PATENT DOCUMENTS 6,312,260 B1    11/2001    Kumar et al.
2002/0168613 A1 *  11/2002    Riley ..................... A61C 1/181
                                                              433/131

(Continued)

FOREIGN PATENT DOCUMENTS

EP    0313222 A2    4/1989
EP    2527059 A1    11/2012
(Continued)

OTHER PUBLICATIONS

International Search Report for Application No. PCT/EP2014/070443 dated Dec. 5, 2014 in 8 pages [the ISR for the PCT Application of this US national phase application].

(Continued)

*Primary Examiner* — Heidi M Eide
(74) *Attorney, Agent, or Firm* — Knobbe Martens Olson & Bear LLP (57) ABSTRACT

The present invention describes a dental kit-of-parts including an implant abutment, a dental restoration and a screw. The head of the screw is provided in a recess formed in the kit-of-parts, with the screw shaft extending through a hole in the implant abutment. A channel in the dental restoration allows access to the screw head by a tool, wherein the diameter of the channel is smaller than the diameter of the screw head. The dental kit-of parts can be manufactured using rapid prototyping such that the captive screw is formed within the combination of the implant abutment and the dental restoration or through conventional means, with (Continued)

the dental abutment and the dental restoration being ex-situ connected to enclose the screw.

4 Claims, 6 Drawing Sheets

(51) Int. Cl.
    *B33Y 10/00*     (2015.01)
    *B33Y 80/00*     (2015.01)
    *A61C 19/02*     (2006.01)

(52) U.S. Cl.
    CPC ........ *A61C 8/0089* (2013.01); *A61C 13/0013* (2013.01); *A61C 13/0018* (2013.01); *A61C 13/0019* (2013.01); *A61C 19/02* (2013.01); *B33Y 10/00* (2014.12); *B33Y 80/00* (2014.12)

(58) Field of Classification Search
    CPC . A61C 13/0018; A61C 13/0019; A61C 19/02; B33Y 10/00; B33Y 8/00
    See application file for complete search history.

(56) References Cited

U.S. PATENT DOCUMENTS

| | | | |
|---|---|---|---|
| 2009/0076508 A1* | 3/2009 | Weinans | A61F 2/30771 606/62 |
| 2010/0297583 A1 | 11/2010 | Benzon et al. | |
| 2010/0311011 A1 | 12/2010 | Schwieder et al. | |
| 2012/0202170 A1 | 8/2012 | Johnson et al. | |
| 2012/0322030 A1 | 12/2012 | Fromovich | |
| 2014/0178836 A1 | 6/2014 | Haus et al. | |
| 2014/0205969 A1* | 7/2014 | Marlin | A61C 8/0001 433/173 |
| 2014/0349250 A1* | 11/2014 | Elsner | A61C 8/005 433/174 |
| 2015/0245890 A1 | 9/2015 | Wouters et al. | |

FOREIGN PATENT DOCUMENTS

| | | |
|---|---|---|
| GB | 2502328 A | 11/2013 |
| GB | 2502331 A | 11/2013 |
| GB | 2518849 A | 4/2015 |
| WO | WO 2001/050978 A1 | 7/2001 |
| WO | WO 2013/004387 A1 | 1/2013 |
| WO | WO 2013/174521 A2 | 11/2013 |
| WO | WO 2013/174524 A1 | 11/2013 |
| WO | WO 2014/095033 A1 | 6/2014 |
| WO | WO 2014/095034 A1 | 6/2014 |
| WO | WO 2016/012581 A1 | 1/2016 |

OTHER PUBLICATIONS

Search and Examination Report for Great Britain Application No. GB1317400.8 dated Apr. 9, 2014 in 5 pages.

* cited by examiner

DENTAL KIT-OF-PARTS AND METHOD OF ASSEMBLING THE SAME

CROSS-REFERENCE TO RELATED APPLICATIONS

This application is a national stage application under 35 U.S.C. § 371 of International Application No. PCT/EP2014/070443, filed on Sep. 25, 2014, which published in English as WO 2015/049149 A1 on Apr. 9, 2015, and which claims priority benefit of GB Patent Application No. 1317400.8, filed on Oct. 1, 2013.

TECHNICAL FIELD

The present invention relates to a dental kit-of-parts for use in dental restoration and a method of manufacturing said dental kit-of-parts.

BACKGROUND ART

Multi-piece osseointegrated dental restorations may consist of an dental implant (also referred to as fixture or implant fixture) that is fixedly implanted into the jawbone, an implant abutment (also referred to as adapter or spacer) that is connected to the dental implant and mediates the connection between the dental implant in the jawbone and a dental restoration (for example a crown or bridge structure), which is the visible, tooth-shaped prosthetics with the functional and aesthetic requirements of that of natural teeth, sitting on top of the dental implant. The combination of implant abutment and dental restoration may also be referred to as dental superstructure, which can be connected to the dental implant via a screw that engages with a thread in the dental implant, thereby mechanically joining the implant and the dental superstructure. The dental restoration is commonly joined to the implant abutment by means of bonding agents like dental cement or adhesives, or via a screw connection. For a more detailed insight into osseointegrated implants, the reader is referred to the standard work: "Osseointegrated implants" by P-I Brånemark, Scandinavian Journal of Plastic and Reconstructive Surgery, Supplement No. 16, 1977, Almquist & Wiksell International (in the following referred to as Reference 1).

In two-piece designs problems may arise from the use of bonding agents in-situ (i.e. in a patient's mouth), where such agents are normally employed in excess to ensure proper closing of an inevitable gap that is formed when the two pieces are joined. Such excess bonding agent may accidentally reach other parts of the implant and could be hard to be removed from there. It can also form inaccessible pockets and cause inflammation or failure of the implant. In addition, in conventional in-situ assembly of dental prosthesis, the screw to connect the dental superstructure to the implant has to be handled separately in the mouth region. This bears the risk of the normally fairly small sized screw getting lost and the patient swallowing or even choking on it. Also, handling a small screw can be bothersome and time consuming. A partial remedy may be the use of one-piece implant as described in WO 2008/138644, where an implant abutment is integrally formed with a screw part, but this may reduce the flexibility of the prosthesis and also limits the number of possible combinations of material that can be used, since normally the one-piece implant is only made of a single material.

Conventionally, the dental restoration is provided with a channel through which the screw is inserted to reach the hole connecting the implant abutment and the implant and also to insert therethrough tools to fasten the screw during assembly. Since it is required that a complete screw can be inserted through the channel, said channels are often rather large compared to the overall size of the dental restoration and thus constitute mechanical weaknesses reducing its robustness and resilience. Furthermore, the channels required equally large exit holes on the surface of the dental restoration which are at least unaesthetic. Additionally, they are also problematic on functional surfaces, for example, on occlusal surfaces, which experience high loads and should thus not possess discontinuities in the form of openings. Hence, the channels are angled relative to a screw axis so that the channel exits on faces of the dental restoration that are less visible and do not bear high loads as described in WO 2008/024062 A2. However, this approach implies that the exit holes are also more difficult to be accessed by the dentist and often special tooling is required that is configured to be inserted through such angulated channels as described in WO 2007/078137 A1.

Problem to be Solved

The present invention seeks to provide a dental kit-of-parts with increased flexibility and adaptability to the individual pre-requisites and needs of a patient alongside with higher ease of handling when the dental kit-of-parts is employed in dental therapy. The above mentioned problems and drawbacks will be addressed by the dental kit-of-parts accordingly.

The problem is solved by the dental kit-of-parts according to claim 1. Further embodiments of the dental kit-of-parts according to claim 1 are described in the respective dependent claims 2 to 17. The problem is further solved by the method of manufacturing a dental kit-of-parts according to claim 18. Embodiments of the method according to claim 18 are described in the respective dependent claims 19 to 24.

BRIEF DESCRIPTION OF FIGURES

The various aspects, features and advantages of the present invention will become apparent from the following description of embodiments and ways of carrying out the invention in combination with the following accompanying drawings, in which.

WAYS OF CARRYING OUT THE INVENTION

Specific embodiments and way of carrying out the invention will now be described in detail with reference to the accompanying drawings. The embodiments are not intended to unduly limit the invention, but are rather provided so that the disclosure will be thorough, complete and will fully convey the scope of the invention to the skilled person. Terminology used in the description is not intended to be limiting the invention either. Further, the drawings are exemplary schematic drawings and not every figure necessarily contains all of the features contained in preceding figures. This is however not to be construed to be limiting or excluding and was done only to highlight additional features and developments. Also, in the drawings, like reference numerals refer to like elements.

Figure 1:
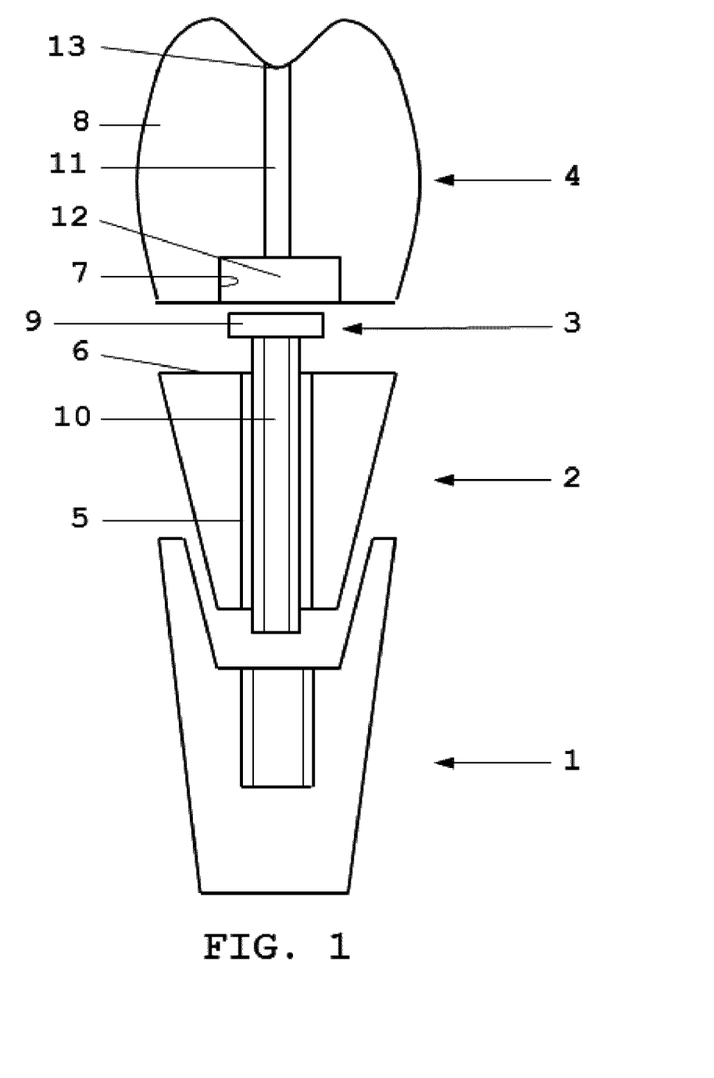
FIG. 1 depicts a schematic, cross-sectional exploded view of a dental kit-of-parts according to one embodiment and a dental implant.

FIG. 1 depicts a schematic, cross-sectional exploded view of a dental kit-of-parts according to one embodiment and a dental implant.

The dental kit-of-parts comprises an implant abutment 2, a dental restoration 4 and a screw 3.

In two-piece designs, the implant abutment 2 is an intermediate, separate piece that mediates a connection between the dental implant 1 fixedly connected to a jawbone and the dental restoration 4. The implant abutment 2 is thus in physical contact with the implant 1, i.e. in abutment with the dental implant 1, and forms a solid foundation for the dental restoration 4. The implant abutment 2 may consist itself of several sub-parts and various designs are conceivable for the details of which it is referred to Reference 1. The present invention is thus not limited to the mere schematic design shown in the drawings. For instance, whilst the drawings show a conical interface between the abutment and the implant, the side walls of the interface need not taper. Additionally, various forms of rotation prevention means can be present, for instance as disclosed in WO 97/10769 A1 or WO 2006/012273 A1. The implant abutment 2 not only provides for a robust and reliable basis for affixing the dental restoration 4, it also confers flexibility and adaptability to the entire dental prosthetics to account for the myriad of dental pre-requisites and needs of each individual patient.

The dental restoration 4 is the aesthetic and functional part of a complete dental prosthesis and connected to the dental implant 1 via the implant abutment 2. As to be described later, there are a number of ways of connecting the dental restoration 4 and the implant abutment 2. Both parts together form a dental superstructure. From an aesthetic viewpoint, the dental restoration 4 should resemble a natural tooth as closely as possible, for example, in color and shape. Basically, when visible, the dental restoration 4 is supposed to be indistinguishable from a natural tooth and should naturally blend in the denture. For labial teeth, the dental restoration 4 should also mimic the incisal translucency of the enamel. From a functional point of view, the dental restoration 4 needs to possess sufficient mechanical strength and durability to enable the patient to fully employ the dental prosthesis for biting and chewing without discomfort or steric limitations. Biting forces can be very high and the dental restoration 4 is so designed as to withstand the loads encountered. In its simplest form, the dental restoration 4 may be in the form of a single tooth, but is however not limited thereto and may further be an array of teeth forming a dental crown.

The screw 3 is a screw suitable for use in dental applications and includes a screw head 9 and a threaded screw shaft 10. In this as well as in all other embodiments, the screw shaft 10 can be threaded over its full or over part of its length. The screw 3 is so designed that a diameter of the screw head 9 is larger than a diameter of the screw shaft 10. In this as well as in all the other depicted embodiments, the diameter is shown as the single outside dimension of a cylindrical screw head in a direction perpendicular to the axis of the shaft. In terms of the invention, however, the term diameter is not to be understood as implying a circular or cylindrical shape. Rather, the outer contour of the screw head 9 when viewed in the direction of the axis of the shaft can be round, polygonal or can have any other regular or irregular shape. This equally applies to the cross-sectional shape of the screw shaft in those parts where there is no thread. The diameter is to be understood as the largest linear dimension across the body of the head, or shaft, of the screw in a direction transverse to the axis of the shaft. The screw head 3 is further configured so that a tool can engage the screw head for performing a rotation of the entire screw 3. The screw 3 is configured to connect a pre-assembly that includes the implant abutment 2 and the dental restoration 4 to an implant 1. The connection is established by the screw shaft 10 being thread engaged with a corresponding thread of a dental implant 1 fixed in the jawbone, whereby the pre-assembly is fixedly positioned in the patient's mouth.

Figure 2:
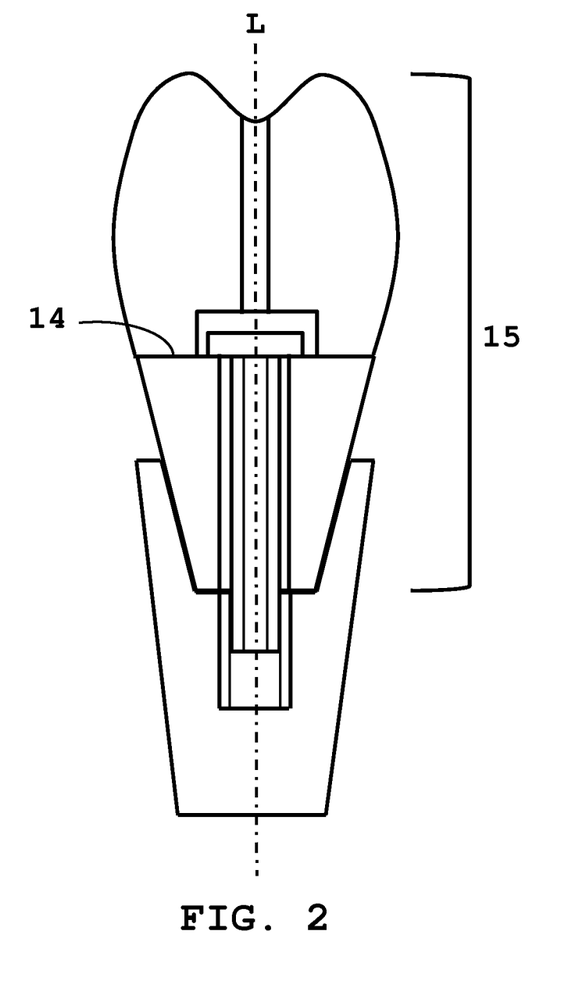
FIG. 2 is a schematic, cross-sectional view of an assembled state of a dental kit-of-parts connected to a dental implant.

A schematic, cross-sectional view of an assembled state of a dental kit-of-parts and an implant 1 as depicted in FIG. 1, is shown in FIG. 2. The dental implant 1 is fixedly connected to a jawbone. The implant abutment 2 is mated with, for instance partially inserted into the dental implant 1, which is so configured to provide a mating part that can accommodate the implant abutment 2. The dental screw 3 is inserted through a through hole 5 formed in the implant abutment 2 and a thread engages with a corresponding part of the dental implant 1. By fastening the screw 3, the screw head 9 abuts a screw seat, here formed by the inner surface 6 of the implant abutment 2, and is pushed towards dental implant 1 and fixedly connected thereto. Furthermore, the dental restoration 4 is connected to the implant abutment 2 via an interface 14 formed therebetween and that interface intersects an outer surface of the pre-assembly. In other words, an interface is formed where the two pieces merge and a joint or seam exists that is exposed to the patient's mouth. The outer surface is to be understood as the outer periphery of the pre-assembly 15 with respect to the mouth, that is to say the buccal and lingual as well as the inter-proximal and coronal sides. The dental restoration 4 comprises a recess 12 configured to accommodate the screw head 9 when the pre-assembly 15 is formed. The dental restoration 4 also includes a channel 11 through which a tool is insertable. The channel has a diameter that is smaller than that of the screw head 9. The channel may further have a diameter larger than that of the screw shaft 10, but that is not necessarily the case. The channel is configured to connect an outer surface 8 of the dental restoration 4 to the recess 12. Here, the outer surface 8 is to be understood as a boundary surface, a periphery, between the patient's mouths and the bulk of the dental restoration 4. In this particular embodiment, both, a longitudinal extension of the channel 11 and a longitudinal axis of the screw shaft 10 coincide with the axis L. The channel's 11 main extension is therefore aligned with the longitudinal axis of the screw shaft 10. Different alignments are also within the scope of this embodiment. In a state where the dental restoration 4 is connected to the implant abutment 2, the screw head 9 is enclosed in the recess, or space, 12 positioned between the implant abutment 2 and the dental restoration 4. In other words, the screw 9 is "trapped" between these two pieces and becomes a captive screw that cannot be lost from the pre-assembly 15.

It is thus preferred that the recess 12 is formed between the two pieces. The term "recess" is not to be understood as requiring any specific way of making it. It is simply a room, space, or enclosure. Further, in that state, a tool can be inserted through and along the channel 11, engage with the screw head 9 and fasten the screw 3. In that state also, the connection between the implant abutment 2 and the dental restoration 4 is established via an inner surface 6 of the implant abutment 2 and an inner surface 7 of the dental restoration 4. As inner surfaces, surfaces are to be construed that are not normally exposed to the patient's mouth, but enclosed by the pre-assembly 15, when the pre-assembly 15 is formed. In other words, these surfaces are internal surfaces of the pre-assembly 15 and as such literally contrary to the outer surface 8.

The interface 14 between the implant abutment 2 and the dental restoration 4 is formed by at least one from the group of, but not limited to: chemical bonding, preferably gluing, bonding and cementing; thermal bonding, preferably laser welding, friction welding; and mechanical bonding, preferably press-fitting, shrink-fitting, screwing and bolting. Accordingly, the interface 14 and mating surfaces of the implant abutment 2 and the dental restoration 4 may comprise layers of dental adhesives or cements, or layers that result from thermal modifications of the adjacent material. In addition, the interface 14 may include mechanical fixing means.

As regards the various parts of the dental kit-of-parts, the parts may comprise a variety of materials from the group of, but not limited to: polymers preferably polymethylmethacrylate, polyurethane, polyether ether ketone; reinforced polymers, preferably reinforced by glass fibers, carbon fibers and/or ceramic particles; dental hybrid ceramics; glass ceramics; titanium and titanium alloys; cobalt chromium alloys; zirconia and alumina. The choice of material depends on the individual part of the kit and further strongly on the needs and prerequisites of the patient and has to made on a case-by-case basis. For example, for temporary dental prosthetics, polymers and/or reinforced polymers are preferred. For long-term prosthetics hybrid ceramics, glass ceramics, the above metals and alloys or oxide ceramics like zirconia and alumina are favored. For the screw 3, high performance steel or even super high performance materials, for instance, amorphous metals are preferred in order to keep the screw as small as possible whilst retaining sufficient mechanical strength for proper fixation. The choice of materials is thus independent of the channel and interface designs as contemplated by the invention.

Similar to the bespoke choice of materials for the parts of the dental kit-of-parts, a suitable way these parts were formed can be selected from, but is not limited to the group of: additive manufacturing, preferably, selective laser melting, selective laser sintering, electron beam melting, direct metal laser sintering, stereolithography, three-dimensional printing and fused deposition modeling; molding, casting and machining.

A related method of manufacturing the above dental kit-of-parts comprises forming the pre-assembly 15 by aligning the implant abutment 2 and the dental restoration 4. Then the screw 3 is positioned between the implant abutment 2 and the two pieces are assembled via the inner surface 6 of the implant abutment and the inner surface 7 of the dental restoration 4, with the screw head 9 positioned in the recess 12 and at least part of the screw shaft 10 accommodated in the through hole 5 of the implant abutment. In that step of forming the pre-assembly 15, the implant abutment 2 and the dental restoration 4 are fixedly connected with the screw head 9 enclosed therein, wherein the implant abutment 2 and the dental restoration 4 are connect by at least one method from the group of: chemical bonding, preferably gluing, bonding and cementing; thermal bonding, preferably laser welding, friction welding and mechanical bonding, preferably press-fitting, shrink-fitting, screwing and bolting. It is preferred that at least the step of forming the pre-assembly is performed ex-situ, i.e., outside a patient's mouth. There is also preferably no temporal relation required between forming the pre-assembly 15 and the dental treatment. Hence, the assembling can be carried-out completely independently to the actual treatment of the patient.

The above dental kit-of-parts and the method of manufacturing the same possess a number of significant advantages over conventional kits and methods.

The channel 11 of the dental restoration 4 is significantly narrower as compared to channels conventionally provided in dental restorations. The latter were formed to not only insert tooling therein, but also to insert the entire dental screw therethrough for it to reach the implant abutment. It was consequently required that the channel be sized so that a screw head can pass through. Due to mechanical restrictions, the screw and screw head cannot be downsized at will, since the screw is a load bearing component and vital for the function and reliability of the prosthesis. Hence, conventionally the channel was rather large compared to the overall dimension of the dental restoration. The rather large discontinuity caused by the channel in the dental restoration significantly impeded its structural integrity and was a potential mechanical weakness. Also, large channels implied rather large exit holes on the surface of the dental restoration. These had aesthetical drawbacks and thus were not formed in the parts of the restoration to be placed in the mouth so that it becomes visible like, for example, labial regions. Thus, such channels were normally required to be angulated so that the exit hole emerged in in regions that are less visible. However, this had as the result that they were also inaccessible for the dentist, therefore requiring special tooling and complicating the dental treatment. Besides the aesthetical disadvantages, large exit holes also ought not to be formed on functional surface of the tooth, for example occlusal faces, due to the high loads there, which require a robust bulk material. The above problems are mitigated by the present invention. The screw 3 is placed inside a two-piece pre-assembly 15, which is then connected so that the screw 3 is enclosed therein. There is thus no need to insert the entire screw through a channel in the dental restoration. The channel 11 is downsized in diameter to a size that suffices for a slim tool to be inserted. Tools made of high strength materials have sufficient stiffness to tighten the screw 3 whilst having a small diameter. Hence, the diameter of the channel 11 can be reduced to an absolute minimum. This means a much smaller exit hole 13 and an increased bulk material cross-section of the dental restoration 4 going along with increased mechanical strength. The much smaller exit hole 13 implies that it is no longer absolutely necessary to position these hole away from visible or functional regions of the teeth, it may in fact be placed again where it is most easily accessible to the dentist. The channel may be angulated or curved, as in the prior art, or straight and on axis, which the prior art sought to avoid, or straight and off axis. The channel can have a cross section which varies or does not vary with along the extension of the channel.

In the dental kit-of-parts, the screw 9 is enclosed in the pre-assembly 15 and becomes a captive screw. Conventional in-situ assembling of two-piece prosthesis with loose screws bears the risk of the normally fairly small sized screw getting lost and/or the patient accidentally swallowing or even worse, chocking on it. Also, handling a small screw can be bothersome and time consuming for the dentist. These drawbacks are overcome by the present invention where the dental screw is captively enclosed in a pre-assembly 15. In the ex-situ method of manufacturing the dental kit, it can be assembled well before the dental treatment and is then transferred to the patient's mouth and connected to the dental implant without the need of having to exercise extra care in handling a small dental screw in-situ. This eases the treatment significantly, reduces treatment time and risks and stress for the patient.

Also, ex-situ assembly of a two-piece design dental prosthesis means that various problems related to the use and processing of bonding agents in-situ, for example, adhesives and dental cements are avoided. The quality of the joint can much more efficiently be achieved outside a patient's mouth and flexibility is higher, since various other joining technologies can be applied that are inapplicable in-situ. Also, the possible issues of having to employ excess bonding agent to assuredly close a gap at the interface between the pieces, which excess bonding agent may flow out, be hard to remove and may even forms inaccessible pockets and cause inflammation and failure of the entire implant, can be avoided when assembling ex-situ as it is the case in the present invention.

Further technical advantages related to ease of use: 1) no mix-up of wrong screw in restoration: 2) enabling good handling as not only screw picks-up, but now the whole restoration can be picked-up with the embedded screw holding the abutment on the screw driver.

Figure 3:
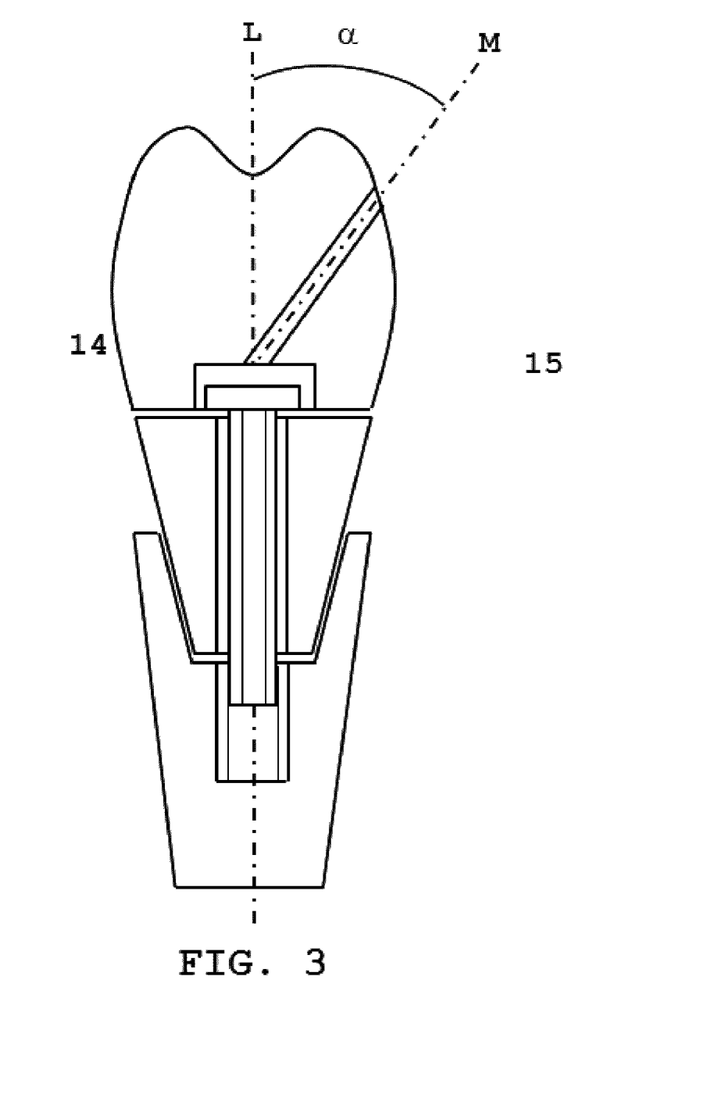
FIG. 3 depicts a schematic, cross-sectional exploded view of a dental kit-of-parts according to another embodiment and a dental implant.

FIG. 3 depicts a schematic, cross-sectional view of a dental kit-of-parts according to another embodiment and a dental implant. Explanations of features identical to those in the previous embodiment will be omitted and only advanced or modified features will be described here.

The dental kit-of-parts according to the present embodiment also includes a dental restoration 4 with an angulated channel 11 whose longitudinal extension, here along a linear axis M, is tilted with respect to the axis L coinciding with a longitudinal axis of the screw shaft 10. This also implies that the exit hole 13 of the channel emerges on a side surface of the dental restoration 4. Preferably, the angle between L and M, i.e., the longitudinal extension of the channel 11 and the axis of the screw shaft 10 is between 0° and 25°.

This embodiment can satisfy the need for providing a flexible dental kit-of-claims that can be adapted to the patient's individual prerequisites and needs that may at times demand the provision of an angulated channel, for instance because its placement in the mouth would otherwise not allow accessing the channel with tools. Aesthetics can be improved and deleterious effects of high chewing forces on the dental restoration 4, when the exit hole 13 emerges, for example, on an occlusal surface, can be further precluded.

Figure 4A:
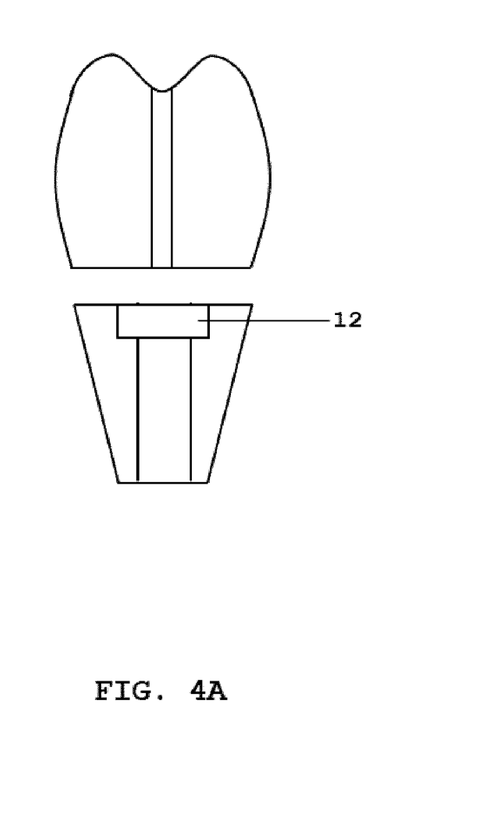
FIGS. 4A and 4B depict a schematic, cross-sectional exploded view of a dental kit-of-parts according to a further embodiment and of that dental kit-of-parts together with a dental implant, respectively.
Figure 4B:
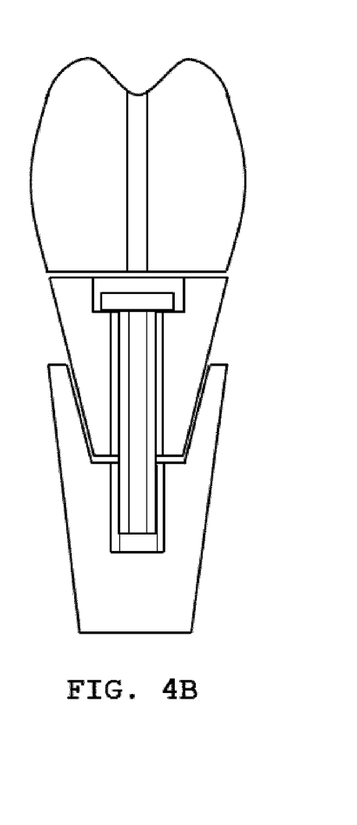

FIGS. 4A and 4B depict a schematic, cross-sectional exploded view of a dental kit-of-parts according to a further embodiment and of that dental kit-of-parts together with a dental implant, respectively. Explanations of features identical to those in the previous embodiments will be omitted and only advanced or modified features will be described here.

As in the above described embodiments, this embodiment comprises a recess 12 in the pre-assembly 15. It is formed between the implant abutment 2 and the dental restoration 4.

Presently, the recess 12 is formed in the implant abutment 2 instead of the dental restoration 4. It thus ought to be evident that the recess can be formed entirely in the abutment, entirely in the restoration, or in both the abutment and the restoration. The direction and course of the channel is independent of the formation of the recess. In the present pre-assembly, the screw 9 is again enclosed by the recess 12 in the implant abutment 2 and the surrounding dental restoration 4, for example, its inner surface 7.

This embodiment confers the dental kit-of-parts additional flexibility and adaptability. Depending on the material selection and the methods employed, it may be preferred and easier to realize the recess 12 in the implant abutment 2.

Figure 5A:
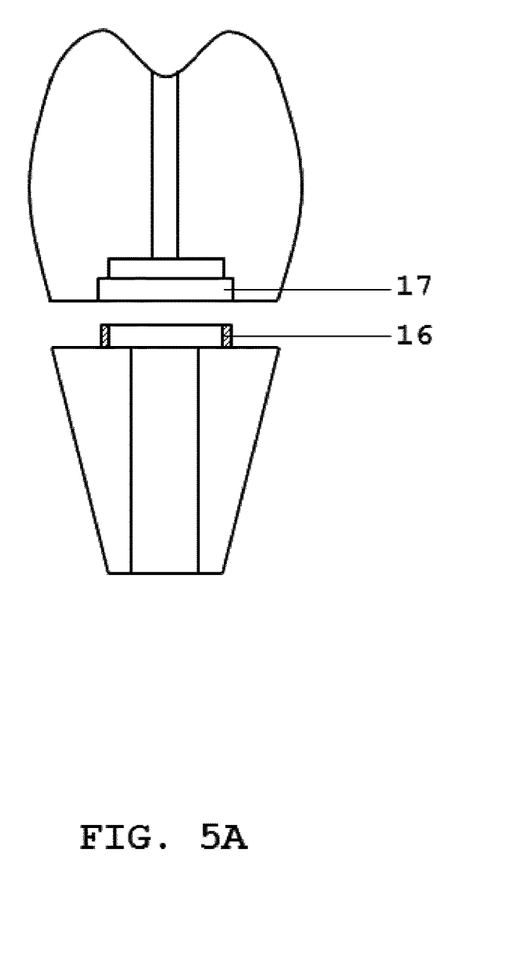
FIGS. 5A and 5B depict a schematic, cross-sectional exploded view of a dental kit-of-parts according to yet another embodiment and of that dental kit-of-parts together with a dental implant, respectively.
Figure 5B:
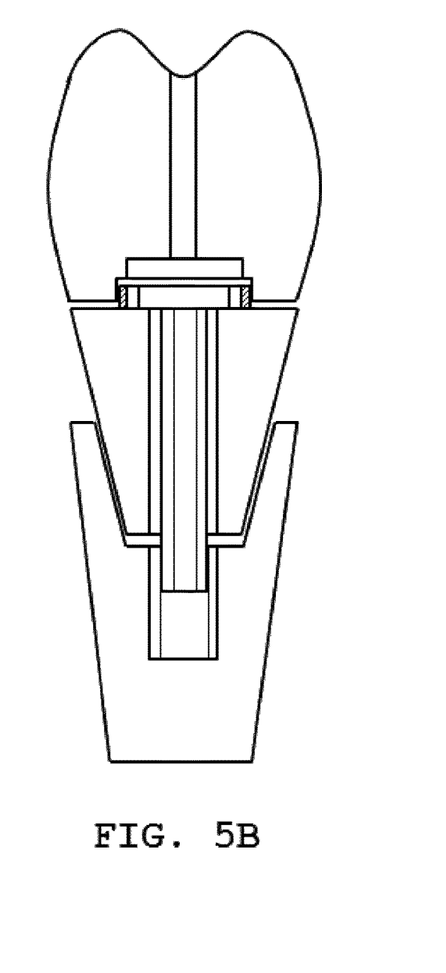

FIGS. 5A and 5B depict a schematic, cross-sectional exploded view of a dental kit-of-parts according to another embodiment and of that dental kit-of-parts together with a dental implant, respectively. Explanations of features identical to those in the previous embodiments will be omitted and only advanced or modified features will be described here.

This embodiment illustrates schematically an alternative way of merging the implant abutment 2 and the dental restoration with the help of assembling means. For instance, the implant abutment 2 is provided with a protrusion 16 and the dental restoration 4 with a receiving section 17. In the pre-assembly 15, these two parts matingly engage each other. In FIG. 5A a male-female configuration is shown, in which the protrusion may have an annular shape and the receiving section 17 so configured as to accommodate the protrusion 16 and to form a form fit, here a circular recess. The receiving section 17 may be integrally formed as part of the recess 12. However, possible configurations are not limited thereto. It is also possible to reverse the male-female configuration, so that the dental restoration 4 comprises a protrusion and the implant abutment 2 the accordingly configured receiving section. In addition, the protrusion 16 and/or the receiving section 17 may comprise alignment and/or rotation prevention features (not shown) so that the pre-assembling is restricted to distinct positions only and degrees of freedom of movement in the mating process and once mated are reduced so as to avoid misassembly or to improve alignment accuracy of the individual pieces. Again, the direction and course of the channel is independent of the other features disclosed by this embodiment.

As said before, in the present embodiment, assembling precision can be improved, since the assembly means restrict the degrees of freedom during forming the pre-assembly 15. Also, time spent on properly aligning the pieces of the dental kit-of-pats is shortened, since the pieces "fall" in the right position almost automatically. Moreover, the form fit increase the strength of the connection between the implant abutment 2 and the dental restoration 4 and may relieve the load bearing interface 14. Consequently, it may also be possible to reduce amounts of bonding agents to be used to connect the pieces of the pre-assembly 15.

Figure 6A:
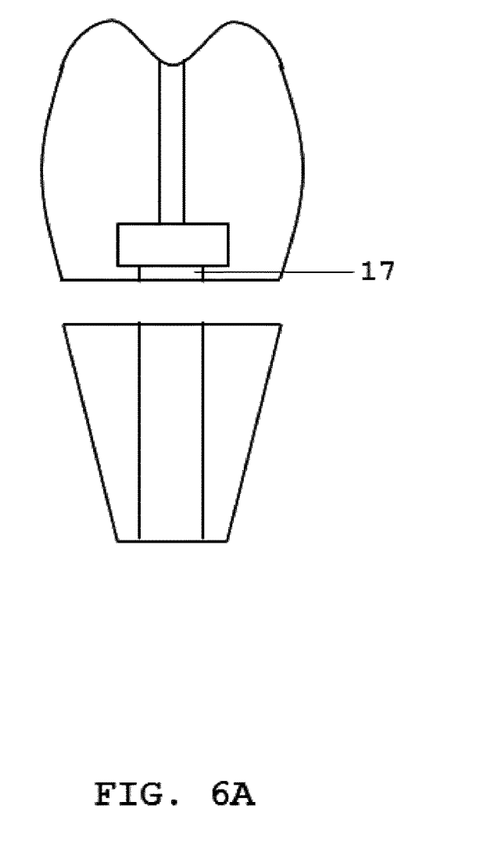
FIGS. 6A and 6B depict a schematic, cross-sectional exploded view of a dental kit-of-parts according to another embodiment and of that dental kit-of-parts together with a dental implant, respectively.
Figure 6B:
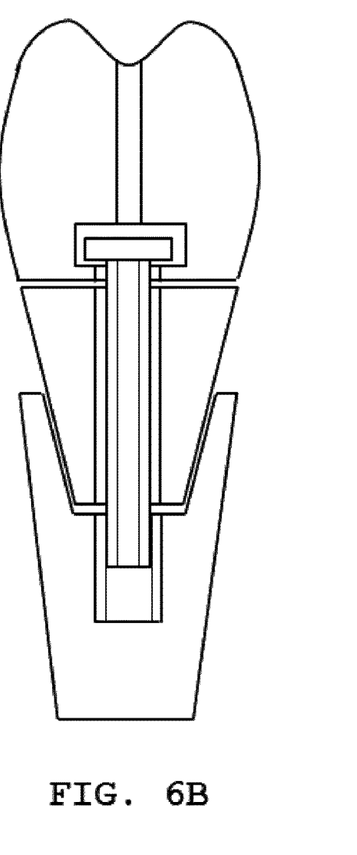

FIGS. 6A and 6B depict a schematic, cross-sectional exploded view of a dental kit-of-parts according to another embodiment and of that dental kit-of-parts together with a dental implant, respectively. Explanations of features identical to those in the previous embodiments will be omitted and only advanced or modified features will be described here.

In this embodiment, the recess 12 that encloses the screw head 9 is formed within the dental restoration 4. This means the recess 12 is enclosed by the dental restoration 4 and has no open sides to a peripheral surface of the dental restoration 4, for example, the inner surface 7. The recess 12 enclosed in the dental restoration 4 is connected to the periphery of the dental restoration 4 via a through hole 18 that is configured to accommodate at least part of the screw shaft 10 therein and has a diameter smaller than a diameter of the screw head 9 and larger than the screw shaft 10. Hence, the screw shaft 10 is partly exposed from the dental restoration 4, but the screw head 9 is trapped therein, so that the screw 9 becomes a captive screw. The face of the recess 12 that is intersected by the through hole 18 serves as a screw seat. In other words, in the present embodiment, a space (recess 12) is formed inside the dental restoration 4, i.e. in the bulk thereof. The screw is so accommodated in the bulk that it is still functional. Functional means that the screw can be operated and used as a connection/fixation means for the dental kit-of-parts. At the same time, the screw is so accommodated in the bulk that it cannot be unintentionally extracted therefrom without destroying at least one of the dental restoration and the screw. The shape, dimensions and design of that space are not particularly limited, as long as the above functionality is ensured.

The dental kit-of-parts according to the present invention preferably also comprises tooling (not shown) configured to adjust and fasten the dental implant 1, the implant abutment 2 and the dental restoration 4. The tooling is not limited to any particular embodiment as long as it achieves the above functionality in dental applications. One example is a simple screw driver to tighten screw 3 via engagement with the screw head 9. Further examples are the Stargrip™ or the Unigrip™ screwdrivers from Nobel Biocare®. More complex tooling is perceivable.

Another preferred embodiment, which is generally combinable with most of the previously mentioned embodiments, is that the screw 3 of the dental kit-of-parts comprises an amorphous metal material and/or an amorphous metal alloy. It is further preferred that said amorphous metal material and/or the amorphous metal alloy is a bulk metallic glass. Moreover, it is preferred that this screw consists of the amorphous metal material or the amorphous metal alloy in bulk. The present preferred embodiment hence defines that the screw 3 used as a connection/fixation means in the dental kit-of-parts is at least partially, or optionally completely, made of an amorphous metal material and/or an amorphous metal alloy, preferably a bulk metallic glass. Non-limiting examples for said materials are: the commercially available "Liquid Metal" and any other biocompatible amorphous metal.

The screw thereby realizes the technical benefits and advantages that go along with the properties of the amorphous metal materials and alloys in dental applications and beyond, for example, but not exclusively: 1) super high elasticity allowing significant higher system pre-load; 2) high corrosion, wear and scratch resistance; 3) a low MRI (Magnetic Resonance Imaging) signature improving MRI-compatibility; 4) possibility of net-shape forming as explained later. The superior mechanical properties allow the transmission of high fastening/connecting forces at reduced load bearing dimensions as compared to conventional metals. By using amorphous metals for the dental screw, the minimal screw dimensions conventionally assumed to be required to bear chewing forces over a life-time and to resist chewing force peaks can be circumvented. Specifically, this implies for the present embodiment that the screw 3 can be generally downsized while maintaining its intended function. Hence, the recess 12 could be reduced in size thereby increasing the load bearing material cross-section, for example, of the dental restoration 4 if formed therein. Also, the holes 5 and 18 can be reduced in size as the screw shaft 10 is reduced in size, which further contributes to the mechanical integrity of the entities in which they are formed. In comparison to conventional metals the friction of the screw is reduced which enables a higher efficiency in converting screwing or tightening torque, i.e. the torque used in fastening the screw, into holding force. Put differently, for the same load bearing capacity as that of a screw connection in conventional metal, a lower screwing torque is required which, in turn, lowers the torque applied to the implant when fastening the screw and achieves benefits in implant stability.

Yet another preferred embodiment, which is also generally combinable with most of the previously mentioned embodiments, is that the tooling comprises an amorphous metal material and/or an amorphous metal alloy. It if further preferred that the amorphous metal material and/or the amorphous metal alloy is preferably a bulk metallic glass. Moreover it is preferred that the tooling consists of the amorphous metal material or the amorphous metal alloy in bulk at least in those parts which engage the screw. This delivers the load-bearing advantages also to the tooling so that mechanical failure of the tooling upon fastening the screw is avoided. The present preferred embodiment hence defines that the tooling configured to adjust and fasten the dental implant, the implant abutment and the dental restoration is at least partially or optionally completely made of an amorphous metal material and/or an amorphous metal alloy, preferably a bulk metallic glass. Examples for said materials and technical benefits realized are at least the ones previously mentioned. Specifically for the present embodiment this implies that the tooling can be significantly downsized, while still being fully functional to ensure proper adjustment and fastening. At the same time, the channel 11 or any opening in the dental kit-of-parts receiving said tooling can be downsized in relation to the downsizing of the tooling. A reduced diameter of the channel 11 increases the mechanical integrity of the dental restoration 4. Furthermore, aesthetic impediments are reduced, since the exit opening of the channel 11 is also reduced in size and hence much less visible.

As indicated above, it is within the scope of this invention that both the screw 3 and the tooling at the same time comprise or consist of an amorphous metal material and/or an amorphous metal alloy, preferably a bulk metallic glass. This combination then results in a dental kit-of-parts, wherein all openings that either receive the screw 3 and/or the tooling, for example 5, 11, 12 and 18, can be reduced in size, hence realizing a beneficial combination of the above mentioned advantages. The minimization of openings in the dental kit-of-parts also allows it to be downsized altogether. Hence, it may, for example, be possible to produce and apply dental restorations, which would, when using conventional screws and tooling, not have enough load bearing material left to be mechanically stable.

There are various possible ways of obtaining the above dental kit-of-parts.

Firstly, the already described method of manufacturing a dental kit-of-parts comprises before the step of forming a pre-assembly additional steps. In this method, the dental restoration 4 is manufactured by a method of additive manufacturing such that the recess 12, the through hole 18 and the channel 12 of the dental restoration 4 are formed within the dental restoration 4. And further, the screw 3 is manufactured simultaneously with the previous step, preferably in-situ with the same production method. This can, for instance be done in a rapid manufacturing machine. The simultaneous manufacturing is performed such that the screw head 9 is formed in the recess 12 and the screw shaft 10 is formed in the though hole 18 of the dental restoration 4 and the screw 3 is a captive screw enclosed by the dental restoration 4. Methods of rapid manufacturing allow for the manufacturing of parts with complicated geometries, for example, with undercuts that are often not at all obtainable by conventional molding and machining. Same applies here. The present embodiment requires a complex tooth-shaped part to be formed, wherein a recess, a through hole, a channel and a screw are to be formed simultaneously with high precision therein. Through the use of rapid manufacturing, the assembly of the dental restoration 4 with enclosed screw 3 can be "grown" layer-by-layer in a bottom-up approach. The resulting piece is an exactly shaped dental restoration with a screw contained therein. The growth process might require the growth of supporting surfaces or ridges that hold the screw 9 during growth, but these are designed as thin as possible so that the screw 9 can be broken loose easily, for example, by inserting a suitable tool through the channel 12 after the growth was completed. Alternatively, the screw can also be chemically released by Aceton or other solvents.

Secondly, before the step of forming a pre-assembly, the following alternative steps are conceivable. During the rapid manufacturing growth of the dental restoration 4, the growth is paused at a stage when the recess 12 is partially formed, for instance for about 50%, and the screw 3 is positioned inside the dental restoration 4 such that the screw head 9 is positioned in the partially grown recess 12 and the screw shaft 10 is at least partially accommodated in the through hole 18. After having inlayed the screw 9, the rapid manufacturing process is continued until the inlayed screw is fully enclosed by the dental restoration and growth of the restoration is completed. In this alternative method, the screw 3 is not necessarily grown simultaneously with the dental restoration 4 or may even not be a part formed by rapid manufacturing. For example, if a screw 3 of a super high strength material, like amorphous metal, that cannot be grown simultaneously via rapid manufacturing, is required, the screw 3 can nevertheless be enclosed in the dental restoration 4 by interrupting the growth, inserting the final screw 3 in the yet to be completed dental restoration 4. The 50% growth is but one of several possible examples for a state in which the screw can still be inserted in the recess 12 and the through hole 18. Growth needs to be paused before the recess 12 starts closing up, i.e. before the dental restoration 4 starts enclosing the recess 12. Within this method and the previous one, modifications are possible. The dental restoration can be grown in an upright position, i.e. the growth direction is substantially the direction of a longitudinal direction of the dental restoration 4 (for example, along axis L in FIG. 2) extending from a cervical base of the dental restoration 4 where the implant abutment 2 will be connected, towards the coronal side of the dental restoration 4. Alternatively, growth can be conducted in a lying position along a transvers axis that is perpendicular to the longitudinal axis, i.e., extends from one of the buccal, lingual, or interproximal surfaces towards an opposite one of the dental restoration 4.

Thirdly, in case the dental restoration 4 is splittable, parting planes maybe formed along the above longitudinal or transversal direction so as to make the recess 12 and the trough hole 18 accessible. A splittable dental restoration 4 maybe achieved a priori by manufacturing two portions of the dental restoration 4 by any suitable method of molding, casting, and/or machining, or by employing rapid manufacturing or any other suitable method to grow a dental restoration 4 with enclosed recess 12, through hole 18 and channel 11, which is then cut by any suitable method along appropriate parting planes into at least two portions so that a screw can be inserted. The portions of the dental restoration may then be re-joined and fixedly connected by any suitable method, preferably at least one from the group of: chemical bonding, preferably gluing, bonding and cementing; thermal bonding, preferably laser welding, friction welding and mechanical bonding, preferably press-fitting, shrink-fitting, screwing and bolting. After joining, the screw 3 is enclosed and thus becomes a captive screw.

The mentioned methods of rapid manufacturing can preferably be at least one from the group of: selective laser melting, selective laser sintering, electron beam melting, direct metal laser sintering, stereolithography, three-dimensional printing and fused deposition modeling. For the alternative method where the rapid manufacturing is paused, fused deposition modeling is more preferably used, since the remaining dental restoration 4 can so be best grown around the inlayed screw 3.

The above embodiment is advantageous in that the screw 3 is enclosed in the dental restoration 4 and as such even further secured against loss. During pre-assembly, handling is eased, since the screw does need to be handled separately and only the dental restoration 4 and the implant abutment 2 need to be merged. Also, the dental restoration 4 and the implant abutment 2 are fixedly connected by screw forces once the screw 3 engages with the dental implant 1. When fastening the screw 3, the screw head 9 imparts a force on the screw seat and pushes the dental restoration 4 and the implant abutment 2 together so that the gap therebetween is closed. This detachable force-fit connection require the use of bonding agents like adhesives or cement and can thus avoid problems related thereto. Advantages of single-piece designs are thus realized. However, bonding agents may still be used to further secure the connection between the two pieces, but the amounts required may be reduced significantly.

In a further preferred method of manufacturing the dental kit-of-parts, in particular, when the screw and/or tooling comprises or consists of an amorphous metal and/or an amorphous metal alloy, the screw and/or the tooling is formed by net shape casting. It is a characteristic of amorphous metals that they do not undergo a significant volume change at solidification. As-casted products are hence close to final products and laborious and expensive post-treatments, for example, finishing such as machining or grinding can be avoided. The present invention therefore provides a particularly efficient method for manufacturing at least certain constituents of the dental kit-of-parts.

Finally, another embodiment is the dental kit-of-parts according to any one of the previously described embodiments also includes a dental implant 1 that is configured to be implanted into a jawbone and tooling that is configured to adjust and fasten the dental implant 1, the implant abutment 2 and the dental restoration 4.

The invention claimed is:

1. Method of manufacturing a dental kit-of-parts, comprising the following steps:
   manufacturing a dental restoration by rapid manufacturing such that a recess and a through hole of the dental restoration are formed within the dental restoration; and
   manufacturing a screw simultaneously with the previous step, such that a screw head is formed in the recess and a screw shaft is formed in the through hole of the dental restoration and the screw is a captive screw enclosed by the dental restoration, wherein the dental restoration has an inner surface and an outer surface, and a channel through which a tool is insertable, the dental restoration being configured to be connected with its inner surface to an inner surface of an implant abutment, the implant abutment being configured to be connected to a dental implant and having a through hole configured to accommodate at least a part of the screw shaft therein, wherein the diameter of the screw head is larger than the diameter of the screw shaft, wherein the kit-of-parts is so configured that the screw can connect a pre-assembly of the implant abutment and the dental restoration to the dental implant, wherein the pre-assembly is so configured as to comprise therein the recess that encloses the screw head, whereby the screw is a captive screw, wherein the channel of the dental restoration connects the outer surface of the dental restoration to the recess and has a diameter smaller than a diameter of the screw head of the screw, and wherein the recess is formed within the dental restoration such that the recess is enclosed by the dental restoration and has no open sides to a peripheral surface of the dental restoration.

2. Method of manufacturing a dental kit-of-parts according to claim 1, wherein the method further comprises:

a step of fixedly connecting the implant abutment and the dental restoration with the screw head enclosed therein, wherein the step of fixedly connecting the implant abutment and the dental restoration comprises at least one step selected from the group of: chemical bonding, gluing, bonding and cementing; thermal bonding, laser welding, friction welding; and mechanical bonding, press-fitting, shrink-fitting, screwing and bolting.

3. Method of manufacturing a dental kit-of-parts according to claim 2, wherein at least the step of fixedly connecting the implant abutment and the dental restoration with the screw head enclosed therein is performed ex-situ.

4. Method of manufacturing a dental kit-of-parts according to claim 1, wherein the method of rapid manufacturing comprises at least one selected from the group of: laser melting, selective laser sintering, electron beam melting, direct metal laser sintering, stereolithography, three-dimensional printing and fused deposition modeling.

* * * * *